United States Patent [19]

Erickson et al.

[11] 4,020,060

[45] Apr. 26, 1977

[54] 7-[α-AMINO-ω-(3,4-METHYLENEDIOXY-PHENYL)ACYLAMIDO]CEPHALOSPORANIC ACID DERIVATIVES

[75] Inventors: Raymond C. Erickson; Ronald E. Bambury, both of Cincinnati, Ohio

[73] Assignee: Richardson-Merrell Inc., Wilton, Conn.

[22] Filed: July 22, 1975

[21] Appl. No.: 598,152

[52] U.S. Cl. .................. 260/243 C; 260/518 R; 424/246

[51] Int. Cl.² ............ C07D 501/36; C07D 501/22; C07D 501/20

[58] Field of Search ........................ 260/243 C

[56] References Cited

UNITED STATES PATENTS

| | | | |
|---|---|---|---|
| 3,489,752 | 1/1970 | Crast | 260/243 C |
| 3,531,481 | 9/1970 | Pfeiffer | 260/243 C |
| 3,673,183 | 6/1972 | Erickson | 260/243 C |
| 3,757,014 | 9/1973 | Crast | 260/243 C |
| 3,796,801 | 3/1974 | Guarini | 260/243 C |
| 3,814,754 | 6/1974 | Jackson | 260/243 C |
| 3,821,198 | 6/1974 | Lee et al. | 260/243 C |
| 3,850,916 | 11/1974 | Crast | 260/243 C |
| 3,864,340 | 2/1975 | Ishimaru et al. | 260/243 C |
| 3,884,914 | 5/1975 | Frazee | 260/243 C |

FOREIGN PATENTS OR APPLICATIONS 24,428 11/1967 Japan

OTHER PUBLICATIONS

Flynn, "Cephalosporins and Penicillins," (1972), pp. 562–563.

*Primary Examiner*—Nicholas S. Rizzo
*Assistant Examiner*—David E. Wheeler
*Attorney, Agent, or Firm*—William J. Stein; Eugene O. Retter; George W. Rauchfuss, Jr.

[57] ABSTRACT

Novel 7-[α-amino-ω-(3,4-methylenedioxyphenyl)acylamido]cephalosporanic acid derivatives are prepared which are useful as antibacterial agents.

11 Claims, No Drawings

7-[α-AMINO-ω-(3,4-METHYLENEDIOXYPHENYL-)ACYLAMIDO]CEPHALOSPORANIC ACID DERIVATIVES

FIELD OF THE INVENTION

The cephalosporin derivatives herein described are particularly useful in the treatment of bacterial infections by oral administration. Methods for their preparation are described.

BACKGROUND OF THE INVENTION

Cephalosporin-type compounds belong to a well-known family of antibiotics which have been widely used in recent years for the treatment of infectious diseases. A number of useful cephalosporins have been obtained by varying the substitution at the 3 and at the 7-positions of the cephalosporin nucleus. The search continues, however, for new compounds having a high order of activity and a high degree of stability.

In an effort to improve and expand upon the existing properties of these compounds, efforts have been directed towards improving the substitution at the 7-position of the cephalosporin nucleus. We have discovered that the presence of an α-amino-ω-83,4-methylenedioxyphenyl)acylamido moiety at the 7-position of a cephalosporin nucleus results in certain novel cephalosporin derivatives having an enhanced activity against one or more gram-positve or gram-negative microorganisms. As antibacterial agens, the compounds of this invention are therapeutically effective in the treatment of infectious diseases due to such gram-positive and gram-negative bacteria in poultry and in animals, including man. Moreover, these compounds are useful as animal feed supplements and as the active ingredient in germicidal preparations employed as surface disinfectants.

PRIOR ART

The semi-synthetic production of 7-acylamidodesacetoxycephalosporin antibiotics from penicillin starting materials has become of importance, due to the process invention of Morin et al. (U.S. Pat. No. 3,275,626) wherein is described a process for converting penicillin sulfoxide esters to desacetoxycephalosopranic acid esters. The preparation of various 7-(α-amino-α-arylacetamido)cephalosporanic acids and the corresponding desacetoxy compounds in which the aryl group can represent a substituted phenyl is described, for example, in U.S. Pat. Nos. 3,489,750, 3,489,751, 3,489,752 and 3,641,021.

Japanese Pat. No. 24428/67 (Farmdoc 29,840T) discloses certain 7-[(substituted)phenylacylamido]-cephalosporanic acids in which the phenyl group is substituted with an alkylenedioxy group.

Belgium 769,609 (Farmdoc 04557T) and Netherlands 7206931 (Farmodoc 79349T) disclose 7-[α-substituted-α-arylacylamino]cephalosporanic acids broadly.

Belgium 776,222 discloses 7-(α-hydroxy-α-phenylacetamido)cephalosporanic acids and 7-(α-amino-α-phenylacetamido)cephalosoproanic acids in which the phenyl ring may be substituted with various groups including hydroxy, halogen, nitro, amino, trifluoromethyl, lower alkyl and lower alkoxy groups.

SUMMARY OF THE INVENTION

This invention relates to novel 7-[α-amino-ω-(3,4-methylenedioxyphenyl)acylamido]cephalosporanic acid derivatives. More particularly, this invention relates to 7-[α-amino-α-(3,4-methylenedioxyphenyl)acylamido]cephalosporanic acid derivatives which are useful as antibacterial agents and which may be represented by the following formula:

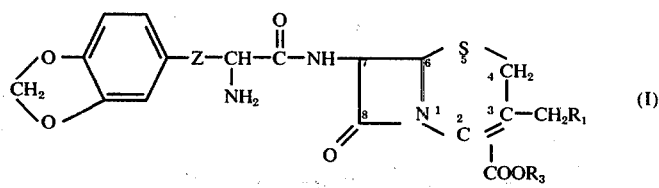

wherein Z is selected from the group consisting of a sigma bond, methylene and ethylene; $R_1$ is selected from the group consisting of hydrogen, hydroxy, acetoxy, pyridinium and $-S-R_2$; $R_2$ is a methyl and ethyl unsubstituted or mono and disubstituted heterocycle selected from the group consisting of pyrazoly, imidazolyl, triazolyl, tetrazolyl, thiazolyl, thiadiazoyl, thuadiazolyl, oxazolyl, isoxazolyl, oxadiazole, pyrimidinyl, pyrazinyl and pyridazinyl; $R_3$ is selected from the group consisting of hydrogen, formyloxymethyl and alkanoyloxymethyl in which the alkanoyl group contains from 1 to 5 carbon atoms; and the pharmaceutically acceptable salts thereof.

The compounds of the present invention are prepared by the condensation of an α-amino-ω-(3,4-methylenedioxypheny) alkanoic acid having the structure:

$$\text{(II)}$$

with a 7-aminocephalosporanic acid having the structure:

$$\text{(III)}$$

wherein Z, $R_1$ and $R_3$ are as defined above, and B is a blocking group selected from the group consisting of t-butyloxycarbonyl, benzyloxycarbonyl, carbomethoxypropen-2-yl, trifluoracetyl, trichloroethoxycarbonyl, p-methoxycarbobenzoxy, p-nitrocarbobenzoxy and the hydrochloric acid salt. These blocking groups are removed after condensation using processes well-known in the art to yield the desired 7-[α-amino-ω-(3,4-methylenedioxyphenyl)acylamido]cephalosporanic acid derivatives of the present invention (1).

Alternatively and preferably, the compounds of the present invention wherein the 3-position of the cephalosporin nucleus is substituted with a heterocyclic thiomethyl group are prepared by the displacement of the 3-acetoxy group of 7-aminocephalosporanic acid with a heterocyclic thiol as illustrated in the following reaction scheme:

The symbol $R_1$ represents the substituents on the 3-methyl group of the cephalosporin nucleus. The compounds obtained when $R_1$ is hydrogen are designated as desacetoxycephalosporanic acids. When $R_1$ is hydroxy, the compounds belong to a class of compounds termed as desacetylcephalosporanic acids. Where $R_1$ represents the acetoxy group, the compounds are designated as cephalosporanic acid derivatives. In the case where $R_1$ represents the pyridinium radical, the 3-position is substituted by a pyridinium methyl group, i.e., the linkage to the pyridine ring is through the heterocyclic nitrogen. Where the 3-position is substituted with hy-

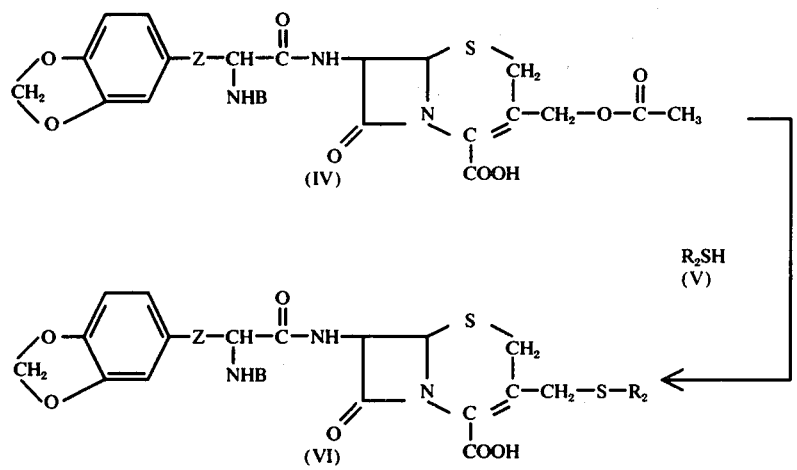

wherein the symbols Z, $R_2$ and B are as defined above. Removal of the blocking group results in the preparation of the compounds of formula (1).

DETAILED DESCRIPTION OF THE INVENTION

As an be seen in formula (1) above all of the compounds of the present invention contain a 1,3-benzodioxole ring at the terminal end of the 7-position acylamido side chains of the cephalosporin nucleus. For purposes of uniformity of nomenclature, however, all of the compounds described herein shall be designated as 3,4-methylenedioxyphenyl derivatives. Additionally, all of the compounds contain a mandatory amino substituent which is alpha in position to the carbonyl function of the amide group.

The acylamido side chain itself can vary from two to four carbon atoms in length as indicated by the symbol Z. Thus, when Z is a sigma bond, the acetamido side chain is delineated and the compounds are designated as 7-[2-amino-2-(3,4-methylenedioxyphenyl)acetamido]cephalosporanic acids. The expression "sigma bond" is intended to refer to the ordinary single bond linkage between two adjacent carbon atoms resulting from the overlap of their corresponding orbitals. When Z is methylene, the 7-[2-amino-3-(3,4-methylenedioxyphenyl)propionamido]cephalosporanic acids are defined, and when Z is ethylene, the 7-[2-amino-4-(3,4-methylenedioxyphenyl)-butyramido]cephalosoporanic acids are defined.

This invention is essentially concerned with the preparation and description of the 7-[αamino-ω-(3,4-methylenedioxyphenyl)acylamido]side chain derivatives of various cephalosporanic acids. These derivatives are readily prepared by condensation at the 7-position of the β-lactam nucleus with any of the readily available 7-aminocephalosporin intermediates.

drogen, the class of compounds are decephalosporanic acids.

The preferred substitution at the 3-methyl position is a heterocyclic thioether as represented by the symbol $-SR_2$. In general, the various heterocyclic groups which are represented by the symbol $R_2$ include five or sixmembered heterocyclic rings containing carbon and one to four atoms selected from the group consisting of nitrogen, oxygen and sulfur. More particularly these heterocyclic rings include pyrazole, imidazole, triazole, tetrazole, thiazole, isothiazole, thiadiazole, oxazole, isoxazole, oxadiazole, pyrimidine, pyrazine and pyridazine and their various isomers. All of the these heterocycles are linked as thioethers at the 3-methyl position. Thus, they are linked via a heterocyclic carbon to the thioether sulfur atom at the 3-position. The heterocyclic groups as represented by $R_2$ may bear one or more lower alkyl groups attached to the remaining heterocyclic ring. The term lower alkyl includes those saturated monovalent hydrocarbon groups having from 1 to 4 carbon atoms as, for example, methyl, ethyl, propyl, isopropyl, butyl, isobutyl and tertiary butyl. Preferably, substitution is with the methyl or ethyl groups and even more preferablu with the methyl group.

The 2-position of the cephalosporin nucleus is substituted with a carboxylic acid or a carboxylic acid ester as indicated by the formyloxymethyl and alkanoyloxymethyl groups. The term alkanoyl as used in this respect includes those groups having a total of from 1 through 5 carbon atoms, as for example, acetyloxy, propionyloxy, butyryloxy, isobutyryloxy, 2-methylbutyryloxy, 3-methylbutyryloxy and 2,2-dimethylpropionyloxy. These esters confer improved properties of absorption upon the molecule and at the same time are physiologically labile. Thus, these esters are readily absorbed from the gastro-intestinal tract and are enzymatically hydrolyzed to the corresponding cephalosporanic acids, thereby providing excellent oral activity.

The pharmaceutically acceptable salts of the compounds of formula (1) include the non-toxic, carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, vinylamine, N,N'-dibenzylethylenediamine, dihydroabietylamine, N-(lower)alkylpiperidine, and additional amines which have been used to form non-toxic salts with benzylpenicillin. These salts can be prepared using conventional means such as contacting and neutralizing a solution of the carboxylic acid in a polar solvent with a stoichiometric quantity of a base.

Also included as pharmaceutically acceptable acid addition salts are the non-toxic organic or inorganic acid addition salts of the base compounds of Formula (1) above. Illustrative inorganic acids which form suitable salts include hydrochloric, hydrobromic, sulfuric and phosphoric acids as well as acid metal salts such as sodium monohydrogen orthophosphate and potassium hydrogen sulfate. Illustative organic acids which form suitable salts include mono, di and tricarboxylic acids, as for example, acetic, glycolic, lactic, pyruvic, malonic, succinic, glutaric, fumarci, malic, tartaric, citric, ascorbic, maleic, hydroxymaleic, benzoic, p-hydroxybenzoic, phenylacetic, cinnamic, salicyclic, 2-phenoxybenzoic and sulfonic acids such as methane sulfonic acid and 2-hydroxyethane sulfonic acid. Such salts can exist in either a hydrated or a substantially anhydrous form.

In addition to the non-toxic carboxylic acid salts and the non-toxic acid addition salts of the basic compounds, the term pharmaceutically acceptable salts is taken to include internal salts or zwitterions of the compounds of formula (1) which are amphoteric in nature. Such zwitterions are pharmaceutically equivalent to either of the above mentioned non-toxic carboxylic acid salts, or the organic and inorganic acid addition salts and also fall within the purview of the present invention.

Stereoisomerism occurs around the asymmetric $\alpha$-carbon atom of these acids. The preferred and most active compounds of the present invention are those having the D-configuration at the $\alpha$-carbon atom in the 7-position side chain and are prepared from the corresponding d (—) -$\alpha$-amino-$\omega$-(3,4-methylenedioxyphenyl)alkanoic acids (11).

Illustrative specific base compounds encompassed by formula (1) above include:

7-[2-amino-2l-(3,4-methylenedioxphenyl)acetamido]cephalosporanic acid, pivaloyloxymethyl 7-[2-amino-2-(3,4-methylenedioxyphenyl)acetamido]cephalosporanate, 7-[2-amino-2-(3,4-methylenedioxyphenyl)acetamido]desacetoxycephalosporanic acid, acetyloxymethyl 7-[2-amino-2-(3,4-methylenedioxyphenyl)acetamido]desacetoxycephalosporanate, 7-[2-amino-2-(3,4-methylenedioxyphenyl)acetamido]desacetylcephalosporanic acid, 7-[2-amino-2-(3,4-methylenedioxyphenyl)aceamido]-3-(pyridiniummethyl)decephalosporanate, formyloxymethyl 7-[2-amino-2-(3,4-methylenedioxyphenyl)acetamido]-3-[(pyrazol-3-ylthio)methyl]-decephalosporanate, 7-[2-amino-2-(3,4-methylenedioxyphenyl)acetamido]-3-[(1-methylpyrazol-3-ylthio)methyl]-decephalosporanic acid, 7-[2-amino-2-(3,4-methylenedioxyphenyl)acetamido]-3-[(5-ethylpyrazol -3-ylthio)methyl]-decephalosoranic acid, 7-[2-amino-2-(3,4-methylenedioxyphenyl)acetamido]-3-[(imidazol-2-ylthio)methyl]decephalosporanic acid, 7-[2-amino-2-(3,4-methylenedioxyphenyl)acetamido]-3-([4-methylimidazol-2-ylthio)methyl]-decephalosporanic acid, acetyloxymethyl 7-[2-amino-2-(3,4-methylenedioxyphenyl) acetamido]-3-[( )1-ethylimidazol-2-ylthio)-methyl]decpehalosporanate, 7-[2-amino-2-(3,4-methylenedioxyphenyl)acetamido]-3-[( 4-ethyl-1,2,3-triazol-5-ylthio)methyl]decephalosporanic acid, 7-[2-amino-2-(3,4-methylenedioxphenyl)acetamido]-3-[(5-methyl-1,2,3-triazol-4-ylthio)methyl]decephalosporanic acid, pivaloyloxymethyl 7-[2-amino-2-(3,4-methylenedioxyphenyl)acetamido]-3-[(1,5-dimethyl-1,2,3-triazol-4-ylthio) methyl]decephalosporanate, 7-[2-amino-2-(3,4-methylenedioxyphenyl)acetamido[-3-[(1-ethyl-1,2,3,4-tetrazol-5-ylthio)methyl]decephalosporanic acid, 7-[2-amino-2-(3,4-methylenedioxyphenyl)acetamido[-3-[(thiazol-4-ylthio)methyl]decephalosporanic acid, 7-[2-amino-2-(3,4-methylenedioxyphenyl)acetamido]-3-[(4-methylthiazol -5-ylthio)methyl]-decehalosporanic acid, formyloxymethyl 7-[2-amino-2-(3,4-methylenedioxyphenyl) acetamido]-3-[(4,5-diethyl-thiazol-2-thio)-methyl]decephalosporanate, 7-[2-amino-2-(3,4-methylenedioxyphenyl)acetamido]-3-[(isothiazol-3-ylthio)methyl]decephalosporanic acid, 7-[2-amino-2-(3,4-methylenedioxyphenyl)acetamido]-3-[(3-methylisothiazol-5-ylthio)methyl]-decephalosporanic acid, 7-[2-amino-2-(3,4-methylendioxyphenyl)acetamido]-3-[(1,2,3-thiadiazol-5-ylthio)methyl]-decephalosporanic acid, 7-[2-amino-2-(3,4-methylenedioxyphenyl)acetamido]-3-[(5-methyl-1,2,3-thiadiazol-4-ylthio)-methyl]decephalosporanic acid, acetyloxymethyl 7-[2-amino-2-(3,4-methylenedioxyphenyl) acetamido]-3-[(1,2,5-thiadiazol-3-ylthio)methyl]decephalosporanate, 7-[2-amino-2-(3,4-methylenedioxyphenyl)acetamido]-3-[(4-ethyl-1,2,5-thiadiazol-3-ylthio)methyl]decephalosporanic acid, 7-[2-amino-2-(3,4-methylenedioxyphenyl)acetamido]-3-[(oxazol-2-ylthio)methyl]decephalosporanic acid, 7-[2-amino-2-(3,4-methylenedioxyphenyl)acetamido]-3-[(4-methyloxazol-5-ylthio)methyl]-decephalosporanic acid, 7-[2-amino-2-(3,4-methylenedioxyphenyl)acetamido]-3-[(4,5-diethyloxazol-2-ylthio)methyl]decephalosporanic acid, pivaloyloxymethyl 7-[2-amino-2-(3,4-methylenedioxyphenyl)acetamido]-3-[(2-methyloxazol-4-ylthio)methyl]decephalosporanate, 7-[2-amino-2-(3,4-methylenedioxyphenyl)acetamido]-3-[(isoxazol-3-ylthio)methyl]decephalosporanic acid, 7-[2-amino-2-(3,4-methylenedioxyphenyl)acetamido]-3-[(4-methylisoxazol-5-ylthio)methyl]decephalosporanic acid, 7-[2-amino-2-(3,4-methylenedioxyphenyl)acetamido]-3-[(3-ethylisoxazol-4-ylthio)methyl]decephalosporanic acid, formyloxymethyl 7-[2-amino-2-(3,4-methylenedioxyphenyl)acetamido]-3-[(1,2,3-oxadiazol-4-ylthio)methyl]decephalosporanate, 7-[2-amino-2-(3,4-methylenedioxyphenyl)acetamido]-3-[(4-methyl-1,2,3-oxadiazol-5-ylthio)methyl]decephalosporanic acid, 7-[2-amino-2-(3,4-methylenedioxyphenyl)acetamido]-3-[(1,2,5-oxadiazol-3-ylthio)methyl]decephalosporanic acid, 7-[2-amino-2-(3,4-methylenedioxyphenyl)acetamido]-3-[(4-ethyl-1,2,5-oxadiazol-3-ylthio)methyl]decephalosporanic acid, 7-[2-amino-2-(3,4-methylenedioxyphenyl)acetamido]-3-[(4-methylpyrimidin-2-ylthio)methyl]decephalosporanic acid, acetyloxymethyl 7-[2-amino-2-(3,4-methylendioxyphenyl)acetamido]-3-[(4,6-diethylpyrimidin-2-ylthio)methyl]decephalosporanate, 7-[2-amino-2-(3,4-methylenedioxyphenyl)acetamido]-3-[(2-methylpyrimidin-5-ylthio)methyl]decephalosporanic acid, 7-[2-amino-2-(3,4-methylenedioxyphenyl)acetamido]-3-[(pyrazin-2-ylthio)methyl]decephalosporanic acid, 7-[2-amino-2-(3,4-methylenedioxyphenyl)acetamido]-3-[(3,5-dimethylpyrazin-2-ylthio)methyl]decephalosporanic acid, pivaloyloxymethyl 7-[2-amino-2-(3,4-methylenedioxyphenyl)acetamido]-3-[(5-methylpyrazin-3-ylthio)methyl]decephalosporanate, 7-[2-amino-2-(3,4-methylenedioxyphenyl)acetamido]-3-[(pyridazin-3-ylthio)methyl]decephalosporanic acid, 7-[2-amino-2-(3,4-methylendioxyphenyl)acetamido]-3-[(5-ethylpyridazin-3-ylthio)methyl]decephalosporanic acid, formyloxymethyl 7-[2-amino-2-(3,4-methylenedioxyphenyl)acetamido]-3-[(6-methylpyridazin-4-ylthio)methyl]decephalosporanate, 7-[2-amino-3-(3,4-methylendioxyphenyl)propionamido]cephalosporanic acid, pivaloyloxymethyl 7-[2-amino-3-(3,4-methylendioxyphenyl)propionamido]cephalosporanate, 7-[2-amino-3-(3,4-methylenedioxyphenyl)propionamido]desacetoxycephalosporanic acid, 7-[2-amino-3-(3,4-methylenedioxyphenyl)propionamido]desacetylcephalosporanic acid, acetyloxymethyl 7-[2-amino-3-(3,4-methylenedioxyphenyl)propionamido]desacetoxycephalosporanate, 7-[2-amino-3-(3,4-methylendioxyphenyl)propionamido]-3-(pyridiniummethyl)decephalosporanate, 7-[2-amino-3-(3,4-methylenedioxyphenyl)propionamido]-3-[(pyrazol-4-ylthio)methyl]decephalosporanic acid, formyloxymethyl 7-[2-amino-3-(3,4-methylenedioxyphenyl)propionamido]-3-[(3-methylpyrazol-4-ylthio)methyl]decephalosporanate, 7-[2-amino-3-(3,4-methylenedioxyphenyl)propionamido]-3-[(1-ethylpyrazol-4-ylthio)methyl]decephalosporanic acid, 7-[2-amino-3-(3,4-methylenedioxyphenyl)propionamido]-3-[(imidazol-4-ylthio)methyl]decephalosporanic acid, 7-[2-amino-3-(3,4-methylenedioxyphenyl)propionamido]-3-[(2-ethylimidazol-4-ylthio)methyl]decephalosporanic acid, acetyloxymethyl 7-[2-amino-3-(3,4-methylenedioxyphenyl)propionamido]-3-[(1-methylimidazol-4-ylthio)methyl]decephalosporanate, 7-[2-amino-3-(3,4-methylenedioxyphenyl)propionamido]-3-[(1,2,4-triazol-5-ylthio)methyl]decephalosporanic acid, 7-[2-amino-3-(3,4-methylenedioxyphenyl)propionamido]-3-[(3-ethyl-1,2,4-triazol-5-ylthio)methyl]decephalosporanic acid, 7-[2-amino-3-(3,4-methylenedioxyphenyl)propionamido]-3-[(4-methyl-1,2,4-triazol-5-ylthio)methyl]decephalosporanic acid, 7-[2-amino-3-(3,4-methylenedioxyphenyl)propionamido]-3-[(1-methyl-1,2,4-triazol-5-ylthio)methyl]decephalosporanic acid, formyloxymethyl 7-[2-amino-3-(3,4-methylenedioxyphenyl)propionamido]-3-[(1,2,3,4-tetrazol-5-ylthio)methyl]decephalosporanate, 7-[2-amino-3-(3,4-methylenedioxyphenyl)propionamido]-3-[(1-methyl-1,2,3,4-tetrazol-5-ylthio)methyl]decephalosporanic acid, 7-[2-amino-3-(3,4-methylenedioxyphenyl)propionamido]-3-[(thiazol-2-ylthio)methyl]decephalosporanic acid, 7-[2-amino-3-(3,4-methylenedioxyphenyl)propionamido]-3-[(4,5-dimethylthiazol-2-ylthio)methyl]decephalosporanic acid, pivaloyloxymethyl 7-[2-amino-3-(3,4-methylenedioxyphenyl)propionamido]-3-[(5-ethylthiazol-4-ylthio)methyl]decephalosporanate, 7-[2-amino-3-(3,4-methylenedioxyphenyl)propionamido]-3-[(3-methylthiazol-5-ylthio)methyl]decephalosporanic acid, 7-[2-amino-3-(3,4-methylenedioxyphenyl)propionamido]-3-[(isothiazol-4-ylthio)methyl]decephalosporanic acid, 7-[2-amino-3-(3,4-methylenedioxyphenyl)propionamido]-3-[(3,5-diethylisothiazol-4-ylthio)methyl]decephalosporanic acid, acetyloxymethyl 7-[2-amino-3-(3,4-methylenedioxyphenyl)propionamido]-3-[(1,2,4-thiadiazol-3-ylthio)methyl]decephalosporanate, 7-[2-amino-3-(3,4-methylenedioxyphenyl)propionamido]-3-[(3-methyl-1,2,4-thiadiazol-5-ylthio)methyl]decephalosporanic acid, 7-[2-amino-3-(3,4-methylenedioxyphenyl)propionamido]-3-[(1,3,4-thiadiazol-2-ylthio)methyl]decephalosporanic acid, pivaloyloxymethyl 7-[2-amino-3-(3,4-methylenedioxyphenyl)propionamido]decephalosporanate, 7-[2-amino-3-(3,4-methylenedioxyphenyl)propionamido]-3-[(oxazol-4-ylthio)methyl]decephalosporanic acid, 7-[2-amino-3-(3,4-methylenedioxyphenyl)propionamido]-3-[(5-methyloxazol-2-ylthio)methyl]decephalosporanic acid, formyloxymethyl 7-[2-amino-3-(3,4-methylenedioxyphenyl)propionamido]-3-[(2,4-dimethyloxazol-5-ylthio)methyl]decephalosporanate, 7-[2-amino-3-(3,4-methylenedioxyphenyl)propionamido]-3-[(1,2,4-oxadiazol-3-ylthio)methyl]decephalosporanic acid, 7-[2-amino-3-(3,4-methylenedioxyphenyl)propionamido]-3-[(5-ethyl-1,2,4-oxadiazol-3-ylthio)methyl]decephalosporanic acid, acetyloxymethyl 7-[2-amino-3-(3,4-methylenedioxyphenyl)propionamido]-3-[(1,3,4-oxadiazol-2-ylthio)methyl]decephalosporanate, 7-[2-amino-3-(3,4-methylenedioxyphenyl)propionamido]-3-[(5-methyl-1,3,4-oxadiazol-2-ylthio)methyl]decephalosporanic acid, 7-[2-amino-3-(3,4-methylenedioxyphenyl)propionamido]-3-[(2-ethyl-1,3,4-oxadiazol-5-ylthio)methyl]decephalosporanic acid, formyloxymethyl 7-[2-amino-3-(3,4-methylenedioxyphenyl)propionamido]-3-[(pyrimidin-2-ylthio)methyl]decephalosporanate, 7-[2-amino-3-(3,4-methylenedioxyphenyl)propionamido]-3-[(5,6-dimethylpyrimidin-2-ylthio)methyl]decephalosporanic acid, pivaloyloxymethyl 7-[2-amino-3-(3,4-methylenedioxyphenyl)propionamido]-3-[(6-ethylpyrimidin-4-ylthio)methyl]decephalosporanate, 7-[2-amino-3-(3,4-methylenedioxyphenyl)propionamido]-3-[(pyrazin-2-ylthio)methyl]decephalosporanic acid, 7-[2-amino-3-(3,4-methylenedioxyphenyl)propionamido]-3-[(3,5-dimethylpyrazin-2-ylthio)methyl]decephalosporanic acid, 7-[2-amino-3-(3,4-methylenedioxyphenyl)propionamido]-3-[(2-methylpyrazin-3-ylthio)methyl]decephalosporanic acid, formyloxymethyl 7-[2-amino-3-(3,4-methylenedioxyphenyl)propionamido]-3-[(pyridazin-3-ylthio)methyl]decephalosporanate, 7-[2-amino-3-(3,4-methylenedioxyphenyl)propionamido]-3-[(3-ethylpyridazin-4-ylthio)methyl]decephalosporanic acid, 7-[2-amino-4-(3,4-methylenedioxyphenyl)butyramido]cephalosporanic acid, acetyloxymethyl 7-[2-amino-4-(3,4-methylenedioxyphenyl)butyramido]cephalosporanate, 7-[2-amino-4-(3,4-methylenedioxyphenyl)butyramido]desacetoxycephalosporanic acid, pivaloyloxymethyl 7-[2-amino-4-(3,4-methylenedioxyphenyl)butyramido]desacetoxycephalosporante, 7-[2-amino-4-(3,4-methylenedioxyphenyl)butyramido]desacetylcephalosporanic acid, 7-[2-amino-4-(3,4-methylenedioxyphenyl)butyramido]-3-(pyridiniummethyl)decephalosporanate, formyloxymethyl 7-[2-amino-4-(3,4-methylenedioxyphenyl)butyramido]-3-[(pyrazol-3-ylthio)methyl]decephalosporanate, 7-[2-amino-4-(3,4-methylenedioxyphenyl)butyramido]-3-[(4,5-dimethylpyrazol-3-ylthio)methyl]decephalosporanic acid, acetyloxymethyl 7-[2-amino-4-(3,4-methylenedioxyphenyl)butyramido]-3-[(1-methylpyrazol-4-ylthio)methyl]decephalosporanate, 7-[2-amino-4-(3,4-methylenedioxyphenyl)butyramido]-3-[(3-ethylpyrazol-4-ylthio)methyl]decephalosporanic acid, 7-[2-amino-4-(3,4-methylenedioxyphenyl)butyramido]-3-[(1-methylpyrazol-5-ylthio)methyl]decephalosporanic acid, 7-[2-amino-4-(3,4-methylenedioxyphenyl)butyramido]-3-[(5-methylpyrazol-2-ylthio)methyl]decephalosporanic acid, 7-[2-amino-4-(3,4-methylenedioxyphenyl)butyramido]-3-[(4-ethylimidazol-2-ylthio)methyl]decephalosporanic acid, pivaloyloxymethyl 7-[2-amino-4-(3,4-methylenedioxyphenyl)butyramido]-3-[(1,4-dimethylimidazol-5-ylthio)methyl]decephalosporanate, 7-[2-amino-4-(3,4-methylenedioxyphenyl)butyramido]-3-[(1,2-dimethylimidazol-4-ylthio)methyl]decephalosporanic acid, 7-[2-amino-4-(3,4-methylenedioxyphenyl)butyramido]-3-[(1,2,3-triazol-5-ylthio)methyl]decephalosporanic acid, 7-[2-amino-4-(3,4-methylenedioxyphenyl)butyramido]-3-[(4-methyl-1,2,3-triazol-5-ylthio)methyl]decephalosporanic acid, formyloxymethyl 7-[2-amino-4-(3,4-methylenedioxyphenyl)butyramido]-3-[(3-ethyl-1,2,4-triazol-5-ylthio)methyl]decephalosporanate, 7-[2-amino-4-(3,4-methylenedioxyphenyl)butyramido]-3-[(1-methyl-1,2,4-triazol-5-ylthio)methyl]decephalosporanic acid, 7-[2-amino-4-(3,4-methylenedioxyphenyl)butyramido]-3-[(1-methyl-1,2,3,4-tetrazol-5-ylthio)methyl]decephalosporanic acid, acetyloxymethyl 7-[2-amino-4-(3,4-methylenedioxyphenyl)butyramido]-3-[(4,5-diethylthiazol-2-ylthio)methyl]decephalosporanate, 7-[2-amino-4-(3,4-methylenedioxyphenyl)butyramido]-3-[(2-methylthiazol-4-ylthio)methyl]decephalosporanic acid, 7-[2-amino-4-(3,4-methylenedioxyphenyl)butyramido]-3-[(4-ethylthiazol 5-ylthio)methyl]decephalosporanic acid, 7-[2-amino-4-(3,4-methylenedioxyphenyl)butyramido]-3-[(4,5-dimethylisothiazol-3-ylthio)methyl]decephalosporanic acid, 7-[2-amino-4-(3,4-methylenedioxyphenyl)butyramido]-3-[(3-ethylisothiazol-4-ylthio)methyl]decephalosporanic acid, 7-[2-amino-4-(3,4-methylenedioxyphenyl)butyramido]-3-[(4-methyl-1,2,3-thiadiazol-5-ylthio)methyl]decephalosporanic acid, 7-[2-amino-4-(3,4-methylenedioxyphenyl)butyramido[-3-[(5-ethyl-1,2,4-thiadiazol-3-ylthio)methyl]decephalosporanic acid, 7[2-amino-4-(3,4-methylenedioxyphenyl)butyramido]-3-[(3-methyl-1,2,5-thiadiazol-4-ylthio)methyl]decephalosporanic acid, pivaloyloxymethyl 7-[2-amino-4-(3,4-methylenedioxyphenyl)butyramido[-3-[(5-ethyl-1,3,4-thiadiazol-2-ylthio)methyl]decephalosporanate, 7-[2-amino-4-(3,4-methylenedioxyphenyl)butyramido[-3-[(5-methyloxazol-2-ylthio)methyl]decephalosporanic acid, 7-[2-amino-4-(3,4-methylenedioxyphenyl)butyramido]-3-[(2,4-dimethyloxazol-5-ylthio)methyl]decephalosporanic acid, 7-[2-amino-4-(3,4-methylenedioxyphenyl)butyramido]-3-[(5-ethylisoxazol-3-ylthio)methyl]decephalosporanic acid, 7-[2-amino-4-(3,4-methylenedioxyphenyl)-butyramido[-3-[(3,4-diethylisoxazol-5-ylthio)methyl]-decephalosporanic acid, formyloxymethyl 7-[2-amino-4-(3,4-methylenedioxyphenyl)butyramido]-3-[(1,2,3-oxadiazol-4-ylthio)-methyl]decephalosporanate, 7-[2-amino-4-methylenedioxyphenyl)butyramido]-3-[(5-methyl-1,2,4-oxadiazol-3-ylthio)methyl]decephalosporanic acid, 7-[2-amino-4-(3,4-methylenedioxyphenyl)-butyramido]-3-[(4-ethyl-1,2,5-oxadiazol-3-ylthio)methyl]decephalosporanic acid, 7-[2-amino-4-(3,4-methylenedioxyphenyl)-butyramido]-3-[(5-methyl-1,3,4-oxadiazol-2-ylthio)methyl]decephalosporanic acid, 7-[2-amino-4-(3,4-methylenedioxyphenyl)-butyramido[-3-[(5-ethylpyrimidin-2-ylthio)methyl]-decephalosporanic acid, 7-[2-amino-4-(3,4-methylenedioxyphenyl)-butyramido[-3-[(2-methylpyrimidin-4-ylthio)methyl]-decephalosporanic acid, acetyloxymethyl 7-[2-amino-4-(3,4-methylenedioxyphenyl) butyramido]-3-[(5-methylpyrazin-2-ylthio)-methyl]decephalosporanate, 7-[(2-amino-4-(3,4-methylenedioxyphenyl)-butyramido]-3-[(5,6-dimethylpyrazin-2-ylthio)methyl]decephalosporanic acid, 7-[2-amino-4-(3,4-methylenedioxyphenyl)-butyramido]-3-[(4-ethylpyridazin-3-ylthio)methyl]-decephalosporanic acid and, 7-[2-amino-4-(3,4-methylenedioxyphenyl)-butyramido]-3-[(5-methylpyridazin-4-ylthio)methyl]-decephalosporanic acid.

The products of the present invention are prepared by reacting 7- aminocephalosporanic acid (III) or a dderivative thereof with an α-amino-ω-(3,4-methylenedioxyphenyl)alkanoic acid (II). The various 7-aminocephalosporanic acids employed as starting materials are well-known compounds which have previously been described in the literature.

Thus, hydrolysis of cephalosporin C results in the formation of 7-aminocephalosporanic acid, Loder et al., Biochem. J. 79, 408–16 (1961) having the formula:

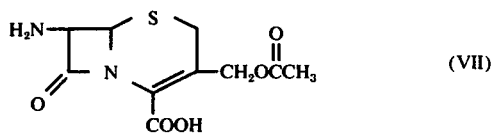

(VII)

The compound 7-aminodesacetoxycephalosporanic acid, which has the formula:

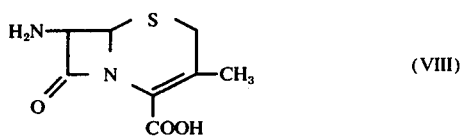

(VIII)

is prepared by the catalytic reduction of cephalosporin C, followed by the hydrolytic removal of the 5-aminoadipoyl side chain as described in U.S. Pat. No. 3,129,224.

Treatment of cephalosporin C with an acetyl esterase prepared from orange peel results in the formation of 3-hydroxymethyl-7-aminodecephalosporanic acid or 7-aminodesacetylcephalosporanic acid (IX), as described by Jeffery et al., Biochem. J., 81, 591 (1961) and having the following formula:

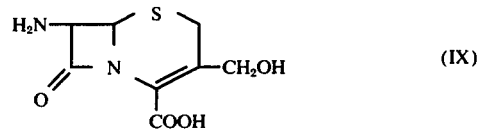

(IX)

Treatment of cephalosporin C with pyridine followed by an acid hydrolysis produces the compound, 7-amino-3-(pyridiniummethyl)decephalosporanic acid (X) as described, for example, in U.S. Pat. No. 3,117,126 and British Pat. Nos. 932,644; 957,570 and 959,054.

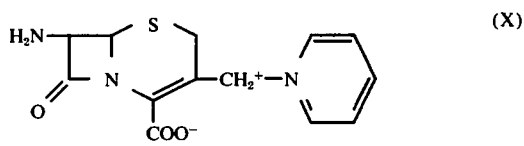

(X)

The 3-thiomethylated 7-aminocéphalospranic acids are obtained by reacting 7-aminocephalosporanic acid with the appropriate thiol as described in U.S. Pat. Nos. 3,516,997 and 3,641,021. The displacement of the acetoxy group in the cephalosporanic acids with a thiol group is a well-known reaction and may be accomplished in aqueous solution at a temperature of from about 25° C. to 150° C. for a period of time ranging from about 15 minutes to 24 hours in the presence of a mild base such as sodium bicarbonate. Preferably an excess of the thiol is employed.

Suitable heterocyclic thiols include the following five or six-membered rings which contain carbon and from one to four atoms selected from the group consisting of nitrogen, oxygen and sulfur, as for example: pyrazole-3-thiol, 5-methylpyrazole-3-thiol, 3,5-dimethylpyrazole-4-thiol, imidazole-2-thiol, imidazole-4-thiol, 1-ethylimidazole-2-thiol, 1,2,3-triazole-4-thiol, 5-methyl-1,2,3-triazole-4-thiol, 1,2,4-triazole-3-thiol, 5-ethyl-1,2,4-triazole-3-thiol, tetrazole-5-thiol, 1-ethyltetrazole-5-thiol, thiazole-2-thiol, 2,4-dimethyltriazole-5-thio, isothiazole-3-thiol, 3,4-diethylisothiazole-5-thiol, 1,2,3-thiadiazole-4-thiol, 5-methyl-1,2,4-thiadiazole-3-thiol, 1,2,5-thiadiazole-3-thiol, 1,3,4-thiadiazole-2-thiol, 5-methyl-1,3,4-thiadiazole-2-thiol, oxazole-2-thiol, 2-ethyloxazole-4-thiol, isoxazole-3-thiol, 3,4-dimethylisoxazole-5-thiol, 1,2,3-oxadiazole-4-thiol, 5-methyl-1,2,4-oxadiazole-3-thiol, 1,2,5-oxadiazole-3-thiol, 3-methylpyrazine-2-thiol, pyridazine-3-thiol and 3-methylpyridazine-4-thiol.

The α-amino-ω-(3,4-methylenedioxyphenyl)alkanoic acids are known compounds. The compound 2-amino-4-(3,4-methylenedioxyphenyl)butyric acid can be obtained from 3(3,4-methylenedioxyphenyl)-propionaldehyde by conversion of the latter compound to the corresponding hydantoin derivative and a subsequent hydrolysis thereof as illustrated in Example 2. Resolution of the racemic α-amino-ω-(3,4-methylenedioxyphenyl)alkanoic acids to their optically active isomers is effected by conversion to the chloroacetmido derivatives and hydrolysis thereof using a hog kidney acylase preparation as shown in Example 1.

The α-amino-ω-(3,4-methylenedioxyphenyl)alkanoic acids are generally coupled as functional equivalents in the form of acylating agents for the primary amino group as indicated in formula II. The symbol B represents a blocking group of the type used either in peptide syntheses or in any of the numerous syntheses of α-aminobenzylpenicillin from 2-phenylglycine. Particularly useful blocking groups include a proton as with the α-amino hydrochloride salt. Alternatively a β-diketo ester, such as methyl acetoacetate, can be employed as disclosed in Great Britain Pat. No. 1,123,333. The blocked amino acid is converted to a mixed anhydride, as for example with ethyl chloroformate, and then condensed with a 7-aminocephalosporanic acid (III). Preferably the blocking group B is selected from the group consisting of t-butyloxycarbonyl, benzyloxycarbonyl, carbomethoxypropen-2-yl, trifluoroacetyl, trichloroethoxycarbonyl, p-methoxy carbobenzoxy,p-nitrocarbobenzoxy and the hydrochloric acid salt.

After coupling, these blocking groups are removed by processes well-known in the art to yield the desired compounds of the present invention. Thus, for example the t-butyloxycarbonyl group can be removed by treatment with trifluoroacetic acid or formic acid, the benzyloxycarbonyl and p-methoxycarbobenzoxy groups can be removed by means of trifluoroacetic acid at room temperature, and the p-nitrocarbobenzoxy group can be removed by catalytic hydrogenation. Obviously, other blocking groups for the α-amino group can also be used and such groups are considered within the scope of the present invention.

Functional derivatives of the α-amino-ω-(3,4-methylenedioxyphenyl)alkanoic acids used in the coupling reaction include the corresponding acyl halides, acid anhydrides, mixed anhydrides, and particularly those mixed anhydrides prepared from stronger acids. Additionally, an acid azide or an active ester or thioester, such as p-nitrophenol, thiophenol or thioacetic acid can be used.

The free α-amino-ω-(3,4-methylenedioxyphenyl)alkanoic acids may also be coupled to the 7-aminocephalosporanic acids (III) by initially reacting the alkanoic acid with N,N'-dimethylchloroformiminium chloride, N,N'-carbonylidiimidazole, N,N'-carbonylditriazole or a carbodiimide. Especially useful carbodiimides include N,N'-dicyclohexylcarbodiimide, N,N'-diisopropylcarbodiimide or N-cyclohexyl-N'-(2-morpholinoethyl)carbodiimide.

The 7-aminocephalosporanic acids (III) can be coupled as a free acid. Preferably, however, they are condensed in the form of suitable salts or readily hydrolyzed esters. Suitable salts include the sodium or trialkylammonium salts in which the alkyl group contains from 1 to 5 carbon atoms. Suitable esters include any of those esters disclosed in U.S. Pat. No. 3,284,451 or any of the silyl esters described in U.S. Pat. No. 3,249,622. Following the coupling reaction, these esters are generally removed to yield the products of this invention. In general, the coupling reaction is conducted in the presence of a suitable solvent such as acetone, dioxane, chloroform, ethylene chloride and tetrahydrofuran. In certain instances, mixtures of water and a miscible organic solvent may be advantageously employed. The temperature of the coupling reaction varies from $-30°$ C. to $100°$ C. with the preferred temperature being at or slightly below room temperature. The reaction time varies anywhere from 15 minutes to as long as 36 hours. Preferably a period of from 1 to 8 hours is employed. Following the condensation reaction, the products are isolated and purified using conventional procedures well-known to those skilled in the art.

A preferred group of compounds (VI) are those containing a methylthioheterocycle group at the 3-position of the cephalosporin nucleus. In addition to the condensation or acylation procedure described above, these compounds can be prepared by the displacement of the 3-acetoxy group of a 7-[α-amino-ω-(3,4-methylenedioxyphenyl)acylamido]cephalosporanic acid (IV) in which the α-amino group may be blocked or unblocked. This displacement or solvolysis is conducted with a substituted or unsubstituted heterocyclic thiol (V), as previously described. The displacement of the acetoxy group as previously described is accomplished in water or buffered aqueous solutions at a temperature ranging from about $25°$ C. to $150°$ C. Preferably, a temperature range of from $50°$ C. to $100°$ C. and a pH of from about 4.0 to 9.0 is employed. Suitable aqueous solutions include those selected from the group consisting of water, or an aqueous solution of acetone, tetrahydrofuran and dimethylformamide.

As indicated, the solvolysis is conducted on a 7-[α-amino-ω-(3,4-methylenedioxyphenyl)acylamido]cephalosporanic acid of formula (IV) in which the α-amino group may be either blocked or unblocked. Suitable blocking groups include those blocking groups earlier mentioned which are represented by the symbol B. A preferred method for conducting the solvolysis reaction is to use a blocked compound of formula (IV) in which the reaction is conducted in essentially the same manner. Subsequent removal of the blocking group is achieved by methods known in the art.

The compounds of this invention include the various cephalosporanic acids, where the symbol $R_3$ is hydrogen and certain esters thereof such as the formyloxymethyl and alkanoyloxymethyl esters wherein the alkanoyl group contains from 1 to 5 carbon atoms. The preferred esters of this invention include the formyloxymethyl, acetyloxymethyl and the pivaloyloxymethyl esters. These esters are generally prepared by condensing an α-amino-ω-(3,4-methylenedioxyphenyl)alkanoic acid of formula (II) with the corresponding 7-aminocephalosporanic ester of formula (III). These esters can be prepared in accordance with the procedures described by Binderup et al., Journal of Antibiotics 24, 767 (1971).

In certain instances the displacement of the acetoxy group from the methyl group at the 3-position results in the migration of the double bond to the 3-position of the β-lactam nucleus. Under those circumstances the position of the double bond can be re-established by the oxidation of the ring sulfur to the sulfoxide with such oxidizing agents as hydrogen peroxide, sodium metaperiodate or an organic peracid. Subsequent reduction of the sulfoxide by means of catalytic hydrogenation or sodium dithionite provides the desired cephalosporin derivatives which are unsaturated in the 2-position of the β-lactam nucleus.

The novel compounds of the present invention are orally and parenterally active having good antibacterial activity. Thus, they are useful antimicrobial agents having a broad spectrum of antimicrobial activity in vitro against standard laboratory microorganisms which are used to screen activity against pathogenic bacteria. The antibacterial spectrum of typical compounds of the present invention can be determined in a standard manner by the agar-dilution streakplate technique commonly used for the testing of new antibiotics.

The presence of the α-amino group in the compounds of this invention has a beneficial effect in increasing and enhancing the spectrum of antimicrobial activity against certain gram-negative microorganisms. Additionally, the presence of the α-amino group imparts certain desirable pharmacological characteistics to the molecule thereby enhancing its oral activity.

The high in vitro antibacterial activity of the novel compounds of this invention not only makes them useful as pharmocological agents pe se, but makes then useful as additives for animal feeds, as well as additives for materials which are subject to microbial deterioration, such as cutting oils and fuel oils. These compounds are also useful for their antibacterial effect in soaps, shampoos and in topical compositions for the treatment of wounds and burns.

The invention described herein is more particularly illustrated in conjunction with the following specific examples.

EXAMPLE 1

D-3,4-Methylenedioxyphenylglycine

A sample of 3,4-methylenedioxyphenylglycine is converted to the chloroacetamido derivative in accordance with the procedure of E. Fisher, Ber., 37, 2486 (1904). Following the procedure of Birnbaum et al., J. Biol. Chem., 194, 455 (1962), the chloroacetylated amino acid is suspended in water and the pH of the suspension is adjusted to 7.5 with 2N lithium hydroxide. The solution is incubated at 37° C. with a hog kidney acylase preparation until hydrolysis of the L-stereoisomer is complete. The pH of the reaction mixture is adjusted to 5.0 and the L-isomer which separates is removed by filtration. The pH of the filtrate is adjusted to 1.0 using concentrated hydrochloric acid and the filtrate extracted with chloroform. The combined chloroform extracts are dried over anhydrous sodium sulfate and evaporated to yield the chloroacetyl derivative of the D-isomer. The chloroacetyl group is removed by hydrolysis using dilute hydrochloric acid. The pH of the hydrolysis mixture is adjusted to 5.5 and the D-3,4-methylenedioxyphenylglycine is collected by filtration.

Following essentially the same procedure the racemic mixtures of 3,4-methylenedioxyphenylalanine and 2-amino-4-(3,4-methylenedioxyphenyl)butyric acid are resolved into their D and L-isomers.

EXAMPLE 2

2-Amino-4-(3,4-methylenedioxyphenyl)butyric acid

A sample of 3-(3,4-methylenedioxyphenyl)propionaldehyde, Mosetig, Ber., 62, 1274 (1929) is converted to the corresponding hydantoin derivative in accordance with the procedure of Henze and Speer, J. Am. Chem. Soc., 64, 522 (1942), by treatment with ammonium carbonate and potassium cyanide. The hydantoin thus obtained is hydrolyzed with barium hydroxide as described in J. Chem. Soc., 1944, 629 to yield the desired 2-amino-4-(3,4-methylenedioxyphenyl) butyric acid.

EXAMPLE 3

N-t-Butyloxycarbonyl-3,4-methylenedioxyphenylglycine

A solution of 1.7 ml. of t-butyloxycarbonylazide in 16 ml. of dioxane is added to a solution of 2 g. of 3,4-methylenedioxyphenylglycine, [prepared in accordance with the procedure of C. Lorenz Ber., 14, 785 (1881)] dissolved in a mixture of 4.2 ml. of triethylamine and 16 ml. of water. The mixture is stirred at room temperature over night and 50 ml. of water is added. The reaction mixture is extracted with ether and the aqueous phase acidified to a pH of 1.5 using dilute hydrochloric acid. The aqueous phase is extracted with ethyl acetate, the combined extracts dried over anhydrous sodium sulfate and evaporated to dryness in vacuo. The residue is triturated with hexane and filtered to yield 2.3 g. of N-t-butyloxycarbonyl-3,4-methylenedioxyphenylglycine, having an m.p. of 120°–3° C.

EXAMPLE 4

3,4-Methylenedioxyphenylalanyl chloride hydrochloride

The compound 3,4-methylenedioxyphenylalanine, Ber., 59, 2952 (1926), is treated with hydrogen chloride and phosphorous pentachloride in accordance with the procedure described by Hartcastle et al., J. Org. Chem., 31, 897 (1966) for the preparation of phenylglycyl chloride hydrochloride to yield 3,4-methylenedioxyphenylalanyl chloride hydrochloride.

EXAMPLE 5

7-[2-Amino-2-(3,4-methylenedioxyphenyl)acetamido] desacetoxycephalosporanic acid A mixture of 2.7 g. of t-butyl-7-aminodesacetoxycephalosporanate, J. Med. Chem. 9, 444 (1966), 2.95 g. of N-t-butyloxycarbonyl-3,4-methylenedioxyphenylglycine, prepared in accordance with Example 3, and 2.5 g. of N-ethoxycarbonyl-2-ethoxy-1,2-dihydroquinoline contained in 50 ml. of chloroform is stirred at room temperature for about 12 hours. The solution is extracted with dilute aqueous hydrochloric acid, followed by extraction with a saturated aqueous solution of sodium bicarbonate, and finally extracted with water. The chloroform solution is dried over anhydrous sodium sulfate and evaporated in vacuo. The solid residue is dissolved in 25 ml. of cold trifluoroacetic acid and the mixture stirred for approximately 20 minutes. The solution is evaporated under reduced pressure to yield a white solid which is washed with ether and dried under vacuum to yield 4 g. of the trifluoroacetate salt of the desired product. The salt is dissolved in 200 ml. of water and an ionexchange resin (basic form) and added thereto in order to remove the trifluoroacetate protecting group. The mixture is stirred until the pH of the solution reaches 5.0. The resin is removed by filtration and the filtrate is concentrated under reduced pressure. The remaining residue is triturated with ethanol and filtered to yield 1.2 grams of 7-[2-amino-2-(3,4-methylenedioxyphenyl)acetamido]desacetoxycephalosporanic acid.

Following essentially the same procedure but substituting 2-N-t-butyloxycarbonyl-3,4-methylenedioxyphenylalanine and 2-N-t-butyloxycarbonylamino-4-(3,4-methylenedioxyphenyl) butyric acid for the 2-N-t- butyloxycarbonyl-3,4-methylenedioxyphenylglycine above, results in the formation of 7-[2-amino-3-(3,4-methylenedioxyphenyl)propionamido]desacetoxycephalosporanic acid and 7-[2-amino-4-(3,4-methylenedioxyphenyl)butyramido] desacetoxycephalosporanic acid.

EXAMPLE 6

7-[2-Amino-3-(3,4-methylenedioxyphenyl)propionamido]cephalosporanic acid

To a slurry of 0.01 mole of 7-aminocephalosporanic acid in 50 ml. of chloroform is added 4 ml. of N,O-bis-trimethylsilylacetamide. The mixture is stirred until all of the solid dissolves and 0.02 moles of N,N-dimethylamine is added. The solution is cooled to 5° C. and a 0.01 mole portion of 3,4-methylenedioxyphenylalanyl chloride hydrochloride is added. The mixture is stirred at 5° to 10° C. for approximately 2 hours under an atmosphere of nitrogen. Fifty milliliters of water are added and the pH of the mixture is brought to 2.0 with an aqueous sodium bicarbonate solution. The aqueous phase is separated, decolorized with charcoal, filtered and the pH of the filtrate is adjusted to 4.0 with a dilute sodium hydroxide solution. The resulting solution is chilled and the desired product which forms is removed by filtration, washed with water and acetone, and air-dried to yield 7-[2-amino-3-(3,4-methylenedioxyphenyl)propionamido]cephalosporanic acid.

Following essentially the same procedure but substituting 3,4-methylenedioxyphenylglycyl cloride hydrochloride and 2-amino-4-(3,4-methylenedioxyphenyl)-butyryl chloride hydrochloride results in the formation of 7-[2-amino-2-(3,4-methylenedioxyphenyl)acetamido]cephalosporanic acid and 7-[2-amino-4-(3,4-methylenedioxyphenyl)butyramido]cephalosporanic acid.

EXAMPLE 7

7-[2-(3,4-methylenedioxyphenyl)acetamido]cephalosporanic acid

A stirred solution of 0.05 mole of N-t-butyloxycarbonyl-3,4-methylenedioxyphenylglycine and 6.9 ml. (0.05 mole) of triethylamine in 200 ml. of tetrahydrofuran is cooled to −10° C. and 6.5 ml. (0.05 mole) of isobutylchloroformate is added. The solution is maintained at a temperature of −10° to −5° C. for approximately 10 minutes, to which is then added with stirring a cold solution of 0.05 mole of the triethylammonium salt of 7-aminocephalosporanic acid, dissolved in 180 ml. of a 50% aqueous tetrahydrofuran solution. The reaction mixture is stirred at 5° C. for approximately one hour and then permitted to come to room temperature for an additional hour. The tetrahydrofuran solvent is removed by evaporation and the residue is dissolved in a mixture of 300 ml. of water and 100 ml. of ethyl acetate. The organic layer is separated and discarded. The aqueous layer is chilled to approximately 5° C. and an additional 300 ml. of ethyl acetate are added. The mixture is acidified to a pH of 3.0 using an aqueous 10% hydrochloric acid solution. The mixture is filtered, the ethyl acetate layer is separated and the aqueous layer is again extracted with 150 ml. of ethyl acetate. The combined organic extracts are washed with water, dried over anhydrous sodium sulfate and evaporated to dryness in vacuo. The residual oil is triturated with a mixture of ether and petroleum ether until it solidifies. Crystallization of this residue from an ether-petroleum ether mixture yields the desired 7-[2-N-t-butyloxycarbonylamino-2-(3,4-methylenedioxyphenyl)acetamido]cephalosporanic acid.

Following essentially the same procedure but substituting 2-N-t-butyloxycarbonyl-3,4-methylenedioxyphenylalanine and 2-N-t-butyloxycarbonylamino-4-(3,4-methylenedioxyphenyl) butyric acid for the N-t-butyloxycarbonyl-3,4-methylenedioxyphenylglycine above, results in the formation of 7-[2-N-t-butyloxycarbonylamino-3-(3,4-methylenedioxyphenyl) propionamido]cephalosporanic acid and 7-[2-N-t-butyloxycarbonyl-amino-amino-4-(3,4-methylenedioxyphenyl)butyramido]cephalosporanic acid, respectively.

EXAMPLE 8

7-[2-Amino-2-(3,4-methylenedioxyphenyl)acetamido]cephalosporanic acid

A 5 gram sample of 7-[2-N-t-butyloxycarbonylamino-2-(3,4-methylenedioxyphenyl)acetamido]cephalosporanic acid, prepared in accordance with Example 7, is dissolved in 40 ml. of anhydrous trifluoroacetic acid which has been previously cooled to 5° C. The resulting solution is stirred for approximately 10 minutes and poured into anhydrous ether. The trifluoroacetic salt which forms is collected by filtration, dissolved in water and the resulting solution stirred with a mildly basic ion-exchange resin until the pH of the solution reaches 5.0. The resin is removed by filtration and the filtrate evaporated to a small volume. The remaining residue is triturated with ethanol, chilled for an hour and the 7-[2-amino-2-(3,4-methylenedioxyphenyl)acetamido]cephalosporanic acid which forms is collected by filtration.

EXAMPLE 9

Pivaloyloxymethyl 7-[2-amino-3-(3,4-methylenedioxyphenyl)propionamide]cephalosporanate hydrochloride Pivaloyloxymethyl 7-aminocephalosporanate hydrochloride (0.01 mole) is suspended with sufficient stirring in 50 ml. of anhydrous chloroform at a temperature of about 0° C. Sodium bicarbonate (2.2 grams) is added, followed by the addition of 3,4-methylenedioxyphenylalanyl chloride hydrochloride (0.01 mole). The mixture is stirred for about 4 hours at 0° C., filtered and the filtrate evaporated to dryness in vacuo. The residue is dissolved in water and lyophilized to yield the desired pivaloyloxymethyl 7-[2-amino-3-(3,4-methylenedioxyphenyl)propionamide]cephalosporanate hydrochloride.

Following essentially the same procedure but substituting formyloxymethyl 7-aminocephalosporanate hydrochloride, acetyloxymethyl 7-aminocephalosporanate hydrochloride and propionyloxymethyl 7-aminocephalosporanate hydrochloride for the pivaloyloxymethyl 7-aminocephalosporanate hydrochloride above results in the formation of formyloxymethyl 7-[2-amino-3-(3,4-methylenedioxyphenyl)propionamido]cephalosporanate hydrochloride, acetyloxymethyl 7-[2-amino-3-(3,4-methylenedioxyphenyl)-propionamido]cephalosporanate hydrochloride and propionyloxymethyl 7-[2-amino-3-(3,4-methylenedioxyphenyl)propionamido]cephalosporanate hydrochloride, respectively.

EXAMPLE 10

Sodium 7-[2-Amino-2-(3,4-methylenedioxyphenyl)acetamido]desacetylcephalosporanate A suspension of 7-[2-amino-2-(3,4-methylenedioxyphenyl)acetamido]cephalosporanic acid, as prepared in Example 8, is suspended in 100 ml. of water, adjusted to a pH of 7.1 with 0.2 N sodium hydroxide solution and treated with orange peel esterase at a pH of 7.0. The pH of the reaction mixture is kept at a constant 7.0 during the reaction by titration with a solution of 0.2 N sodium hydroxide. After approximately 4 hours, the resulting solution is treated with activated carbon, and filtered through a pad of diatomaceous earth. The pad is extracted with an aqueous 80% acetone solution and the extract is evaporated in vacuo to remove the acetone. The resulting aqueous solution is lyophilized to yield the desired sodium 7-[2-amino-2-(3,4-methylenedioxyphenyl)acetamido]-desacetylcephalosporanate.

Following essentially the same procedure but substituting the compounds 7-[2-amino-3-(3,4-methylenedioxyphenyl)propionamido]cephalosporanic acid and 7-[2-amino-4-(3,4-methylenedioxyphenyl)-butyramido]cephalosporanic acid for the 7-[2-amino-2-(3,4-methylenedioxyphenyl)acetamido]cephalosporanic acid above results in the formation of the sodium salts of 7-[2-amino-3-(3,4-methylenedioxyphenyl)propionamido]desacetylcephalosporanic acid and 7-[2-amino-4-(3,4-methylenedioxyphenyl)butyramido]-desacetylcephalosporanic acid, respectively.

EXAMPLE 11

7-[2-Amino-2-(3,4-methylenedioxyphenyl)acetamido]-3-(pyridiniummethyl)decephalosporanate N-t-butyloxycarbonylamino-3,4-methylenedioxyphenylglycine, as prepared by the procedure of Example 3, is dissolved in dry tetrahydrofuran containing triethylamine. The solution is cooled in an ice bath, and isobutyl chloroformate in dry tetrahydrofuran is added dropwise with stirring. After approximately 20 minutes, an aqueous cold solution of 7-amino-3-(pyridiniummethyl)decephalosporanic acid is added dropwise over a period of 30 minutes. The mixture is stirred with cooling for three hours. Cold water is added and the tetrahydrofuran removed in vacuo. The remaining aqueous solution is over-layered with ethyl acetate and acidified to a pH of 2.5 using 1N hydrochloric acid The aqueous layer is evaporated to dryness in vacuo. The amorphous residue is dissolved in methanol, filtered, and concentrated to induce crystallization. The resulting product so obtained is treated with trifluoroacetic acid in order to remove the N-t-butyloxycarbonyl amino protecting group yielding the desired 7-[2-amino-2-(3,4-methylenedioxyphenyl)acetamido]-3-(pyridiniummethyl)decephalosporanate.

Following essentially the same procedure but substituting 2-N-t-butyloxycarbonyl-3,4-methylenedioxyphenylalanine and 2-N-t-butyloxycabonyl amino-4-(3,4-methylenedioxyphenyl)butyric acid for the 2-N-t-butyloxycarbonyl-3,4-methylenedioxyphenylglycine above results in the preparation of 7-[2-amino-3-(3,4-methylenedioxyphenyl)propionamido]-3-(pyridiniummethyl)decephalosporanate and 7-[2-amino-4-(3,4-methylenedioxyphenyl)butyramido]-3-(pyridiniummethyl)decephalosporanate, respectively.

EXAMPLE 12

7-Amino-3-[(1-methyl-1,2,3,4-tetrazol-5-ylthio)methyl]decephalosporanic acid To a mixture of 7-aminocephalosporanic acid and 1-methyl-1,2,3,4-tetrazole-5-thiol contained in a 50% aqueous acetone solution, is added sodium bicarbonate until all of the reactants are completely dissolved. The resulting solution is stirred for approximately 6 hours at 60° C. and concentrated to dryness under reduced pressure. The residue is dissolved in water and the pH of the resulting solution is adjusted to 4.0 with a 10% hydrochloric acid solution to form a precipitate which is removed by filtration and washed with alcohol to yield the desired 7-amino-3-[(1-methyl-1,2,3,4-tetrazol-5-ylthio)methyl]decephalosporanic acid.

Following essentially the same procedure but substituting 5-methyl-1,3,4-thiadiazole-2-thiol, 1,2,3-triazole-5-thiol, 5-methyl-imidazole-2-thiol and 1,3,4-oxadiazole-2-thiol for the 1-methyl-1,2,3,4-tetrazole-5-thiol above results in the formation of 7-amino-3-[(5-methyl-1,3,4-thiadiazol-2-ylthio)methyl]decephalosporanic acid, 7-amino-3-[(1,2,3-triazol-5-ylthio)methyl]decephalosporanic acid, 7-amino-3-[(5-methyl-imidazol-2-ylthio)methyl]decephalosporanic acid and 7-amino-3-[(1,3,4-oxadiazol-2-ylthio) methyl]decephalosporanic acid, respectively.

EXAMPLE 13

7-[2-Amino-3-(3,4-methylenedioxyphenyl)propionamido]-3-[(1,2,3-triazol-5-ylthio)methyl]decephalosporanic acid To a stirred and cooled (5 + 2° C.) suspension of 0.05 mole of 7-amino-3-[(1,2,3-triazol-5-ylthio)methyl]-decephalosporanic acid is added 150 ml. of methylene chloride, 13.5 ml. (0.092 mole) of triethylamine, 15 ml. (0.118 mole) of N,N-dimethylaniline and 19.1 ml. (0.15 mole) of trimethylchlorosilane. The reaction mixture is cooled for approximately 15 minutes and then brought to its reflux temperature for a period of about 25 minutes. On cooling to 5° C., 3,4-methylenedioxyphenylalanyl chloride hydrochloride (0.061 mole) is added. The reaction mixture is stirred at about 10° C. for one hour, 150 ml. of water are added, stirring continued for an additional 15 minutes and the mixture filtered. The aqueous phase is separated and its pH adjusted to 2.0 using a 10% aqueous sodium hydroxide solution. The aqueous solution is filtered and the pH of the filtrate adjusted to 4.0 with 10% sodium hydroxide. The aqueous phase is extracted with ether, separated, filtered and 50 ml. of acetonitrile added. The mixture is cooled, and the desired 7-[2-amino-3-(3,4-methylenedioxyphenyl)propionamido]-3-[(1,2,3-triazol-5-ylthio)methyl]decephalosporanic acid is collected by filtration, washed with water and dried under vacuum. Following essentially the same procedure, but substituting 7-amino-3-[(1-methyl-1,2,3,4-tetrazol-5-ylthio)methyl]decephalosporanic acid, 7-amino-3-[(5-methyl-1,3,4-thiadiazol-2-ylthio)-methyl]decephalosporanic acid, 7-amino-3-[(5-methylimidazol-2-ylthio)methyl]decephalosporanic acid and 7-amino-3-[(1,3,4-oxadiazol-2-ylthio)methyl]decephalosporanic acid in lieu of the 7-amino-3-[(1,2,3-triazol-5-ylthio)methyl]decephalosporanic acid above results in the formation of 7-[2-amino-3-

(3,4-methylenedioxyphenyl)propionamido]-3-[(1-methyl-1,2,3,4-tetrazol-5-ylthio)methyl]decephalosporanic acid, 7-[2-amino-3-(3,4-methylenedioxyphenyl)propionamido]-3-[(5-methyl-1,3,4-thiadiazol-2-ylthio)methyl]decephalosporanic acid, 7-[2-amino-3-(3,4-methylenedioxyphenyl)propionamido]-3-[(5-methylimidazol-2-ylthio)methyl]decephalosporanic acid, and 7-[2-amino-3-(3,4-methylenedioxyphenyl)propionamido]-3-[(1,3,4-oxadiazol-2-ylthio)methyl]-decephalosporanic acid, respectively.

Substituting 3,4-methylenedioxyphenylglycyl chloride hydrochloride and 2-amino-4-(3,4-methylenedioxyphenyl)butyryl chloride hydrochloride for the 3,4-methylenedioxyphenylalanyl chloride hydrochloride above results in the formation of 7-[2-amino-2-(3,4-methylenedioxyphenyl)acetamido]-3-[(1,2,3-triazol-5-ylthio)methyl]decephalosporanic acid and 7-[2-amino-4-(3,4-methylenedioxyphenyl)butyramido]-3-[(1,2,3-triazol-5-ylthio)methyl]decephalosporanic acid, respectively.

EXAMPLE 14

7-[2-Amino-2-(3,4-methylenedioxyphenyl)acetamido]-3-[(5-methyl-1,3,4-thiadiazol-2-ylthio)-methyl]decephalosporanic acid A mixture of 7-[2-N-t-butyloxycarbonylamino-2-(3,4-methylenedioxyphenyl)acetamido]cephalosporanic acid (0.036 mole), 2-mercapto-5-methyl-1,3,4-thiadiazole(0.038 mole), sodium bicarbonate (0.038 mole) and 33 ml. of phosphate buffer (pH 6.2) is heated at 57° C. for a period of about 23 hours. The solution is cooled to room temperature and extracted with ethyl acetate. The aqueous phase is further cooled to 5° C., additional ethyl acetate is added thereto and the mixture is stirred with the addition of 3N hydrochloric acid to adjust the pH to 3.0. The organic phase is separated and the aqueous layer re-extracted with ethyl acetate. The organic extracts are combined, dried over anhydrous sodium sulfate and evaporated under reduced pressure. The residue which remains is dissolved in an aqueous 5% sodium bicarbonate solution, treated with charcoal, filtered and acidified to yield the N-t-butyloxycarbonyl derivative of the desired product. This derivative is dissolved in cold trifluoroacetic acid (10 g. of acid per 1 g. of compound) and the mixture is allowed to stand for about 15 minutes. The resulting acidic solution is poured into ten volumes of anhydrous ether and the trifluoroacetate salt which precipitates is collected by filtration and washed with ether. The trifluoroacetate salt is dissolved in a minumum of water and the pH of the solution is adjusted to 4.0 with a dilute solution of ammonium hydroxide. The desired 7-[2-amino-2-(3,4-methylenedioxyphenyl)acetamido]-3-[(5-methyl-1,3,4-thiadiazol-2-ylthio)methyl]decephalosporanic acid which separates is collected by filtration and dried. Following essentially the same procedure but substituting 5-mercapto-1-methyl-1,2,3,4-tetrazole, 4-mercapto-1,2,3-triazole, 2-mercapto-5-methyl-imidazole and 2-mercapto-1,3,4-oxadiazole for the 2-mercapto-5-methyl-1,3,4-thiadiazole above results in the formation of 7-[2-amino-2-(3,4-methylenedioxyphenyl)acetamido]-3-[(1-methyl-1,2,3,4-tetrazol-5-ylthio)methyl]decephalosporanic acid, 7-[2-amino-2-(3,4-methylenedioxyphenyl)acetamido]-3-[(1,2,3-triazol-5-ylthio)methyl]decephalosporanic acid, 7-[2-amino-2-(3,4-methylenedioxyphenyl)acetamido]-3-[(5-methylimidazol-2-ylthio)methyl]decephalosporanic acid and 7-[2-amino-2-(3,4-methylenedioxyphenyl)acetamido]-3-[(1,3,4-oxadiazol-2-ylthio)methyl]decephalosporanic acid, respectively.

Following essentially the same procedure but substituting 7-[2-N-t-butyloxycarbonylamino-3-(3,4-methylenedioxyphenyl)propionamido]cephalosporanic acid and 7-[2-N-t-butyloxycarbonylamino-4-(3,4-methylenedioxyphenyl)butyramido]cephalosporanic acid for the 7-[2-N-t-butyloxycarbonylamino-2-(3,4-methylenedioxyphenyl)acetamido]cephalosporanic acid above results in the formation of the corresponding 7-[α-amino-ω-(3,4-methylenedioxyphenyl)acylamido]cephalosporanic acid.

EXAMPLE 15

The following example illustrates the in vitro activity of the compounds of this invention.

Two-fold serial dilutions of the test compound are made in trypticase soy broth. A series of tubes of both containing different concentrations of the test compound are inoculated with the particular bacterial culture used for in vitro activity. The inoculated tubes are examined for the inhibition of bacterial growth after 24 hours of incubation at 37° C. The following table summarizes the minimal inhibitory concentration (MIC) for the various bacterial cultures tested with the compound 7-[2-amino-2-(3,4-methylenedioxyphenyl)acetamido]desacetoxycephalosporanic acid.

| Organism | MIC (mcg/ml) |
| --- | --- |
| Diplococcus pneumoniae | 3.1 |
| Staphylococcus aureus | 1.6 |
| Streptococcus pyogenes | 0.8 |
| Escherichia coli | 50.0 |
| Salmonella schottmuelleri | 50.0 |

EXAMPLE 16

The following example illustrates the in vivo activity of the compounds of this invention.

Several groups of 10 mice are challenged with a fatal bacterial infection. Various dose levels of the test compound are administered orally or subcutaneously to separate groups of these animals 1 and 4 hours after challenge. After three or four days, depending upon the test organism, the number of survivors are recorded at each dose level and the dose required per treatment to protect fifty percent of the infected mice ($ED_{50}$) is calculated by the method described by Reed and Muench, Amer. J. Hyg. 27, 493–497 (1938).

| | $ED_{50}$ (mg/kg/dose) Route of Administration | |
| --- | --- | --- |
| Organism | per os | subcutaneous |
| Diplococcus pneumoniae | 45 | 40 |
| Streptococcus pyogenes | 1.0 | 0.9 |
| Salmonella schottmuelleri | — | 26 |

We claim:
1. A 7-[α-amino-ω-(3,4-methylenedioxyphenyl)acylamido]cephalosporanic acid having the formula:

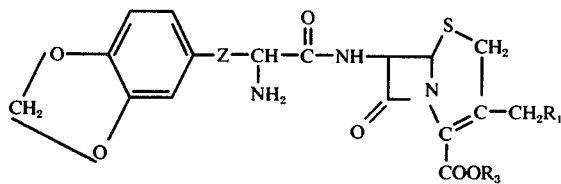

wherein
Z is selected from the group consisting of a sigma bond, methylene and ethylene;
R₁ is selected from the group consisting of hydrogen, hydroxy, acetoxy, pyridinium and —S—R₂;
R₂ is a heterocycle selected from the group consisting of pyrazolyl, imidazolyl, triazolyl, tetrazolyl, thiazolyl, isothiazolyl, thiadiazolyl, oxazolyl, isoxazolyl, oxadiazole, pyrimidinyl, pyrazinyl, pyridazinyl and the mono or di-methyl and mono or diethyl derivatives thereof;
R₃ is selected from the group consisting of hydrogen, formyloxymethyl and alkanoyloxymethyl in which the alkanoyl group contains from 1 to 5 carbon atoms; and the pharmaceutically acceptable salts thereof.

2. A compound in accordance with claim 1, having the formula:

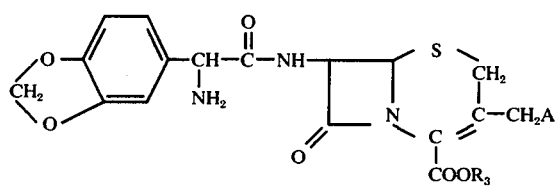

wherein
A is selected from the group consisting of hydrogen, hydroxy, acetoxy and pyridinium;
R₃ is selected from the group consisting of hydrogen, formyloxymethyl and alkanoyloxymethyl in which the alkanoyl group contains from 1 to 5 carbon atoms; and the pharmaceutically acceptable salts thereof.

3. A compound in accordance with claim 1 having the formula:

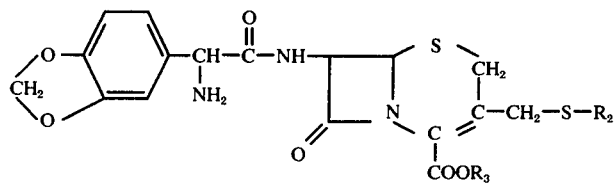

wherein
R₂ is a heterocycle selected from the group consisting of pyrazolyl, imidazolyl, triazolyl, tetrazolyl, thiazolyl, isothiazolyl, thiadiazolyl, oxazolyl, isoxazolyl, oxadiazole, pyrimidinyl, pyrazinyl, pyridazinyl and the mono or di-methyl and mono or di-ethyl derivatives thereof;
R₃ is selected from the group consisting of hydrogen, formyloxymethyl and alkanoyloxymethyl in which the alkanoyl group contains from 1 to 5 carbon atoms; and the pharmaceutically acceptable salts thereof.

4. A compound of claim 1 which is 7-[2-amino-2-(3,4-methylenedioxyphenyl)acetamido]desacetoxycephalosporanic acid.

5. A compound of claim 1 which is 7-[2-amino-2-(3,4-methylenedioxyphenyl)acetamido]cephalosporanic acid.

6. A compound of claim 1 which is 7-[2-amino-2-(3,4-methylenedioxyphenyl)acetamido]-3-[(5-methyl-1,3,4-thiadiazol-2-ylthio)methyl]decephalosporanic acid.

7. A compound of claim 1 which is 7-[2-amino-2-(3,4-methylenedioxyphenyl)acetamido]-3-[(1-methyl-1,2,3,4-tetrazol-5-ylthio)methyl]decephalosporanic acid.

8. A compound of claim 1 which is 7-[2-amino-2-(3,4-methylenedioxyphenyl)acetamido]-3-[(1,2,3-triazol-5-ylthio)methyl]decephalosporanic acid.

9. A compound of claim 1 which is 7-[D-2-amino-2-(3,4-methylenedioxyphenyl)acetamido]-3-[(5-methyl-1,3,4-thiadiazol-2-ylthio)methyl]decephalosporanic acid.

10. A compound of claim 1 which is 7-[D-2-amino-2-(3,4-methylenedioxyphenyl)acetamido]-3-[(1-methyl-1,2,3,4-tetrazol-5-ylthio)methyl]decephalosporanic acid.

11. A compound of claim 1 which is 7-[D-2-amino-2-(3,4-methylenedioxyphenyl)acetamido]-3-[(1,2,3-triazol-5-ylthio)methyl]decephalosporanic acid.

* * * * *

UNITED STATES PATENT AND TRADEMARK OFFICE
CERTIFICATE OF CORRECTION

PATENT NO. : 4,020,060
DATED : April 26, 1977
INVENTOR(S) : Raymond C. Erickson and Ronald E. Bambury It is certified that error appears in the above-identified patent and that said Letters Patent are hereby corrected as shown below:

Column 1, line 36, "α-amino-ω-83,4-" should read "α-amino-ω-(3,4-"; Column 2, line 1, "arylacylamino" should read "arylacylamido"; Column 2, lines 34-35, "thiazolyl, thiadiazoyl, thuadiazolyl, oxazolyl," should read "thiazolyl, isothiazolyl, thiadiazolyl, oxazolyl,"; Column 4, line 56, "preferablu" should read "preferably"; Column 5, line 30, "fumarci," should read "fumaric,"; Column 5, line 52, "d (-) -α-" should read "D (-) -α-"; Column 5, line 56, "7-[2-amino-2]-(3,4-" should read "7-[2-amino-2-(3,4-"; Column 5, line 66, "aceamido" should read "acetamido"; Column 6, line 15, "([4-methylimidazol-" should read "[(4-methylimidazol-"; Column 6, line 18, "-3-[()1-" should read "-3-[(1-"; Column 6, line 19, "decpehalosporanate" should read "decephalosporanate"; Column 6, line 23, "methylenedioxphenyl" should read "methylenedioxyphenyl"; Column 6, lines 30 and 33, "acetamido[-3-" should read "acetamido]-3-"; Column 6, line 39, "thiazol-2-thio" should read "thiazol-2-ylthio"; Column 9, line 51, "desacetoxycephalosporante" should read "desacetoxycephalosporanate"; Column 10, lines 52, 58 and 61, "butyramido[-3-" should read "butyramido]-3-"; Column 11, lines 2, 17 and 20, "butyramido[-3-" should read "butyramido]-3-"; Column 11, line 25, "7-[(2-amino-" should read "7-[2-amino-"; Column 11, line 36, "dderivative" should read "derivative"; Column 12, line 26, "7-aminocephalospranic" should read "7-aminocephalosporanic"; Column 15, line 32, "(1962)" should read "(1952)"; Column 17, line 40, "7-[2-(3,4-methylenedioxy" should

UNITED STATES PATENT AND TRADEMARK OFFICE
CERTIFICATE OF CORRECTION

PATENT NO. : 4,020,060                    Page 2 of 2
DATED : April 26, 1977
INVENTOR(S) : Raymond C. Erickson and Ronald E. Bambury It is certified that error appears in the above–identified patent and that said Letters Patent are hereby corrected as shown below:

read "7-[2-N-t-Butyloxycarbonylamino-2-(3,4-methylenedioxy"; Column 18, lines 11-12, "butyloxycarbonyl-amino-amino-4-" should read "butyloxycarbonylamino-4-"; Column 18, lines 40-41, "propionamide" should read "propionamido"; Column 18, line 52, "propionamide" should read "propionamido".

Signed and Sealed this

Twentieth Day of December 1977

[SEAL]

Attest:

RUTH C. MASON
*Attesting Officer*

LUTRELLE F. PARKER
*Acting Commissioner of Patents and Trademarks*